United States Patent
Heuer et al.

(10) Patent No.: US 7,314,897 B2
(45) Date of Patent: Jan. 1, 2008

(54) AROMATIC FORMALS AS ADDITIVES FOR LOWERING THE WATER UPTAKE OF POLYCARBONATES

(75) Inventors: Helmut-Werner Heuer, Krefeld (DE); Rolf Wehrmann, Krefeld (DE); Friedrich-Karl Bruder, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 408 days.

(21) Appl. No.: 10/921,398

(22) Filed: Aug. 19, 2004

(65) Prior Publication Data

US 2005/0090593 A1    Apr. 28, 2005

(30) Foreign Application Priority Data

Aug. 23, 2003  (DE)  ............................... 103 38 909

(51) Int. Cl.
*C08K 5/06* (2006.01)
(52) U.S. Cl. .................. 524/366; 524/369; 524/370; 524/372; 524/378
(58) Field of Classification Search ............... 524/366, 524/369, 370, 372, 378
See application file for complete search history.

(56) References Cited

U.S. PATENT DOCUMENTS

| | | | |
|---|---|---|---|
| 4,299,636 A | * | 11/1981 | Hartman et al. ............ 149/19.4 |
| 4,374,974 A | | 2/1983 | Hay ............................. 528/219 |
| 6,441,123 B1 | | 8/2002 | Hariharan et al. .......... 528/196 |

FOREIGN PATENT DOCUMENTS

| | | |
|---|---|---|
| EP | 54 488 | 2/1984 |
| GB | 1116589 | 6/1968 |

OTHER PUBLICATIONS

Database CA 'Online! Chemical Abstracts Service, Columbus, Ohio, US: Tanimoto, Shiego et al: "A facile preparation of benzaldehyde diaryl acetals" XP002307253 gefunden im STN Database accession No. 90:6036 Zusammenfassung & Bulletin of the Institute for Chemical Research, Kyoto University, 56(3), 101-3 Coden: Bicras; ISSN: 0023-6071, 1978.
Bull. Inst. Chem. Res. Kyoto Univ., vol. 56, No. 6, (month unavailable) 1978, pp. 297-299.
Shigeo Tanimoto et al, "Syntheses of Formaldehyde Diaryl Acetals and Dithioacetals in the Presence of 18-Crown-6 Catalyst".

* cited by examiner

*Primary Examiner*—Edward J. Cain
(74) *Attorney, Agent, or Firm*—Noland J. Cheung; Aron Preis; Robert S. Klemz

(57) ABSTRACT

A thermoplastic molding composition comprising polycarbonate and at least one aromatic formal is disclosed. The formal conforms to

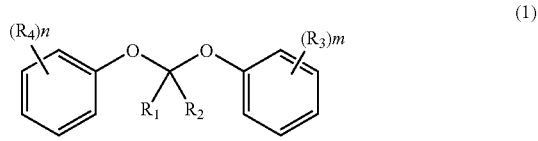

(1)

The composition that is characterized by its reduced water uptake, is useful especially for the production of optical data carriers, such as compact discs.

9 Claims, No Drawings

AROMATIC FORMALS AS ADDITIVES FOR LOWERING THE WATER UPTAKE OF POLYCARBONATES

FIELD OF THE INVENTION

The invention concerns thermoplastic molding compositions and in particular that contain aromatic polycarbonates.

SUMMARY OF THE INVENTION

A thermoplastic molding composition comprising polycarbonate and at least one aromatic formal is disclosed. The formal conforms to

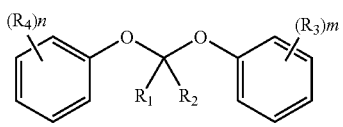
(1)

The composition that is characterized by its reduced water uptake, is useful especially for the production of optical data carriers, such as compact discs.

TECHNICAL BACKGROUND OF THE INVENTION

The Application relates to new aromatic formals, thermoplastic molding compositions comprising polycarbonate and at least one aromatic formal according to the invention as an additive for lowering the water uptake of the polycarbonate and for improving the flowability, and the use of such molding compositions for the production of molded articles, in particular optical data carriers, such as e.g. compact discs, video discs, digital versatile discs and further optical data carriers which may be written to and deleted once or several times, and the corresponding molded articles themselves.

Polycarbonates are employed generally, because of their particular combination of properties, such as transparency, heat resistance and dimensional stability, as materials for injection molding or injection-compression molding of optical data carriers. To improve the processability, processing in general taking place at temperatures in the range from 300° C. to 400° C., additives such as mold release agents and stabilizers are as a rule added to the polycarbonate.

Aromatic polycarbonates based on bisphenol A are used in particular for the production of optical data carriers. However, they may absorb up to 0.34 wt. % of water, which may have an adverse effect on the dimensional stability of the data carriers. An improved dimensional stability is of importance, however, especially if blue or blue-green lasers are employed.

U.S. Pat. No. 6,391,418 describes substrates for data carrier media which comprise a biphenyl derivative as an additive for increasing the dimensional stability (lower shrinkage).

The addition of small amounts of m-terphenyl to bisphenol A polycarbonate, which leads to a reduction in the water uptake, is described in M. Ueda, Mitsubishi Engineering Plastics Corp., Technical Digest of Joint ISOM/ODS 2002 Waikoloa Hi., 8.7.2002, pages 33-35. The disadvantage of these biphenyl derivatives, however, is that they are highly conjugated aromatic π systems which already absorb in the blue or blue-green spectral region. This is undesirable in storage technologies which operate in this wavelength range. Furthermore, terphenyls are relatively rigid molecules, which has an adverse effect on the mechanical properties in the mixture with polycarbonate.

The possibilities described in the prior art thus do not lead to satisfactory results in every respect. However, no indication at all that formals could be suitable as additives is to be found in the prior art.

There was therefore the object of providing thermoplastic molding compositions which comprise polycarbonate with a reduced water uptake and as a result have a better dimensional stability. In particular, the new disc formats with a relatively high storage capacity and-possibly a thinner disc thickness, such as e.g. digital versatile discs (DVDs), require a higher heat stability compared with the CD. Damage to the material occurring during processing to molded articles and the formation of a deposit in the mold become more critical. It is thus desirable that an additive for reducing the water uptake at the same time has the effect of a lowering of the melt viscosity and therefore a better flow at somewhat lower temperatures.

With the molding compositions according to the invention, this object is surprisingly achieved by an improved quality of the data storage medium and an improved processability of the material in injection molding or the injection-compression molding process and a reduced water uptake and therefore improved dimensional stability.

The present Application therefore provides thermoplastic molding compositions comprising at least one polycarbonate and at least one aromatic formal according to the invention with a specific chemical structure as an additive for reducing the water uptake. These aromatic formals thus lead to an improved dimensional stability of the data carriers and at the same time have the effect of a lower melt viscosity.

In contrast to polycarbonate, aromatic polyformals may be prepared in a homogeneous phase from bisphenols and methylene chloride in the presence of alkali metal hydroxides. In this polycondensation, methylene chloride functions simultaneously as a reactant and as a solvent. U.S. Pat. No. 4,374,974 describes a process in which, starting from specific bisphenols, linear and cyclic oligo- and polyformals may be obtained after reaction with methylene chloride. The conversion of monofunctional phenols to low molecular weight aromatic formals by means of this synthesis variant is not described in the prior art.

S. Tanimoto et al., Bull. Inst. Chem. Res., Kyoto Univ., vol. 56, no. 6, 1978 discloses a synthesis in DMSO or acetonitrile in the presence of 18-crown-6 for certain methyl-, chloro-, bromo- and methoxy-substituted species as a new possible use for this phase transfer catalyst. However, nothing is said about the synthesis of further formals or the usability thereof.

DETAILED DESCRIPTION OF THE INVENTION

The aromatic formals according to the invention are based on the general formula

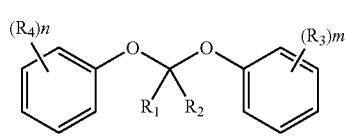
(1)

wherein
$R_1$ and $R_2$ represent hydrogen or phenyl,
$R_3$ and $R_4$ independently of one another represent hydrogen, linear or branched $C_1$-$C_{40}$-alkyl or -alkoxy, preferably $C_1$ to $C_{32}$-alkyl or -alkoxy, particularly preferably $C_1$ to $C_{28}$-alkyl or -alkoxy, very particularly preferably $C_1$ to $C_{26}$-alkyl or -alkoxy and especially very particularly preferably $C_1$ to $C_{24}$-alkyl or -alkoxy, optionally substituted $C_6$ to $C_{14}$-aryl or -aryloxy, preferably $C_6$ to $C_{10}$-aryl or -aryloxy, or $C_7$ to $C_{30}$-aralkyl, particularly preferably $C_7$ to $C_{24}$-aralkyl, and n and m independently of one another represent an integer between 0 and 5, preferably 1 to 3, particularly preferably 1 to 2 and very particularly preferably 1, it also being possible for these to be isomer mixtures.

Compounds of the formula (1) in which at least one of the radicals $R_3$ and $R_4$ independently of one another is selected from the alkyl substituents defined above are also preferred.

Compounds of the formula (1) in which at least one of the radicals $R_3$ and $R_4$ independently of one another is selected from the alkoxy substituents defined above are also preferred.

Compounds of the formula (1) in which at least one of the radicals $R_3$ and $R_4$ independently of one another is selected from the aryl substituents defined above are also preferred.

Compounds of the formula (1) in which at least one of the radicals $R_3$ and $R_4$ independently of one another is selected from the aryloxy substituents defined above are also preferred.

Compounds of the formula (1) in which at least one of the radicals $R_3$ and $R_4$ independently of one another is selected from the aralkyl substituents defined above are also preferred.

The aromatic formals are very particularly preferably described by the general formula (2)

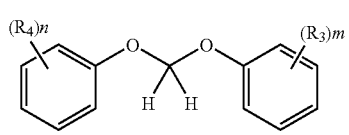

wherein $R_3$, $R_4$, m and n have the abovementioned meanings, it also being possible for these to be isomer mixtures.

The compounds of the formulae (1) and (2) in which $R_3$ and $R_4$ have the same meaning are furthermore very particularly preferred.

The present invention furthermore relates to a process for the preparation of formals of the formulae (1) and (2), characterized in that a monofunctional phenol or a mixture of monofunctional phenols of the formula

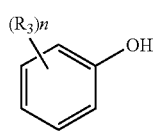

wherein $R_3$ and n have the abovementioned meanings, are reacted in a homogeneous solution of methylene chloride or α,α-dichlorotoluene and a suitable high-boiling solvent, such as, for example, N-methylpyrrolidone (NMP), dimethylformamide (DMF), N-methylcaprolactam (NMC), chlorobenzene, dichlorobenzene or tetrahydrofuran (THF), in the presence of a base, preferably sodium hydroxide (NaOH) or potassium hydroxide (KOH) and very particularly NaOH, preferably at temperatures of between 30 and 80° C., particularly preferably between 50 and 80° C. and very particularly preferably between 60 and 80° C. Preferred high-boiling solvents are NMP, DMF and NMC, particularly preferably NMP and NMC and very particularly preferably NMP.

The phenols of the formula (3) are known or may be prepared by processes known from the literature, for example by Friedel-Crafts alkylation (Organikum, Organisch-chemisches Grundpraktikum, corrected reprint of the 20th edition, Wiley-VCH, Weinheim, p. 355, 1999). Very many phenols are also commercially obtainable (suppliers e.g. Aldrich, Fluka, Acros etc.). It is also being possible to use the phenols of formula (3) as isomer mixtures or as a mixture of various phenols of the formula (3).

The molding compositions according to the invention in general comprise the aromatic formals in a content of 10-60,000 ppm, preferably 10-50,000 ppm, particularly preferably 20-40,000 ppm, very particularly preferably between 50 and 30,000 ppm.

Embodiments which make use of the parameters, compounds, definitions and explanations mentioned under preferred, particularly preferred or very particularly preferred are preferred, particularly preferred or very particularly preferred.

The definitions, parameters, compounds and explanations mentioned generally in the description or mentioned in preferred ranges, however, may also be combined with one another as desired, that is to say between the particular ranges and preferred ranges.

The invention furthermore provides the use of such molding compositions for the production of optical data carriers, such as e.g. compact discs, video discs, digital versatile discs and further optical data carriers which may be written to and deleted once or several times, and the optical data carriers themselves which may be produced from the polymer mixtures.

The molding compositions may of course also be used for other traditional polycarbonate uses, including in those which use a polycarbonate with a relatively high molecular weight. The uses may be transparent or opaque, such as, for example: foodstuffs and drinks packaging, optical lenses and prisms, lenses for illumination purposes, automobile headlamp lenses, glazing for construction and motor vehicles and panes of another type, such as for greenhouses, so-called twin-wall sheets or hollow sheets. Other examples of the uses are profiles, films, all types of housings, e.g. for medical equipment and domestic appliances, such as juice presses, coffee machines and mixers; for office machines, such as computers, monitors, printers and copiers; for sheets, pipes, electrical installation conduits, windows, doors and profiles for the construction sector, interior fitting-out and exterior uses; and in the electrical engineering field, e.g. for switches and plugs. The molded articles according to the invention may furthermore be used for interior fittings and components of track vehicles, ships, aircraft, buses and other motor vehicles and for motor vehicle body parts.

Thermoplastic molding compositions in the context of the present invention predominantly comprise aromatic polycarbonates. Polycarbonates are to be understood as meaning both homopolycarbonates and copolycarbonates; the polycarbonate may be linear or branched in a known manner. They have a weight-average molecular weight, determined by gel permeation chromatography, of 5,000 to 80,000, preferably 10,000 to 40,000. The molecular weight is particularly preferably between 15,000 and 35,000, in particular 15,000 and 22,000.

These polycarbonates are prepared in a known manner from diphenols, carbonic acid derivatives, optionally chain terminators and optionally branching agents.

Details of the preparation of polycarbonates have been laid down in many patent specification for about 40 years. Reference may be made here by way of example only to Schnell, "Chemistry and Physics of Polycarbonates", Polymer Reviews, volume 9, Interscience Publishers, New York, London, Sydney 1964, to D. Freitag, U. Grigo, P. R. Müller, H. Nouvertne', BAYER AG, "Polycarbonates" in Encyclopedia of Polymer Science and Engineering, volume 11, second edition, 1988, pages 648-718 and finally to Dres. U. Grigo, K. Kirchner and P. R. Müller "Polycarbonate" in Becker/Braun, Kunststoff-Handbuch, volume 3/1, Polycarbonate, Polyacetale, Polyester, Celluloseester, Carl Hanser Verlag Munich, Vienna 1992, pages 117-299.

Compounds which are suitable for the preparation of the polycarbonates are, for example, hydroquinone, resorcinol, dihydroxydiphenyls, bis-(hydroxyphenyl)-alkanes bis-(hydroxyphenyl)-cycloalkanes, bis-(hydroxyphenyl) sulfides, bis-(hydroxyphenyl) ethers, bis-(hydroxyphenyl) ketones, bis(hydroxyphenyl) sulfones, bis-(hydroxyphenyl)-sulfoxides, α,α'-bis-(hydroxyphenyl)-diisopropylbenzenes and nucleus-alkylated and nucleus-halogenated compounds thereof.

Preferred diphenols are 4,4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl) sulfone, 2,4-bis-(3,5-dimethyl-4-hydroxyphenyl)-2-methylbutane, 1,4-bis-[2-(4-hydroxyphenyl)-2-propyl]benzene, 2,2-bis-(3,5-dichloro-4-hydroxyphenyl)-propane, 2,2-bis-(3,5-dibromo-4-hydroxyphenyl)-propane, 1,1-bis-(4-hydroxyphenyl)-3,3,5-trimethylcyclohexane and 1,3-bis-[2-(4-hydroxyphenyl)-2-propyl]benzene.

Particularly preferred diphenols are 2,2-bis-(4-hydroxyphenyl)-propane (BPA), 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, 1,3-bis-[2-(4-hydroxyphenyl)-2-propyl]-benzene (BPM), 1,1-bis-(4-hydroxyphenyl)-cyclohexane and 1,1-bis-(4-hydroxyphenyl)-3,3,5-trimethylcyclohexane (TMC).

These and further suitable diphenols are described e.g. in U.S. Pat. Nos. 3,028,635, 2,999,835, 3,148,172, 2,991,273, 3,271,367, 4,982,014 and 2,999,846, in DE-A 1 570 703, 2 063 050, 2 036 052, 2 211 956 and 3 832 396, French Patent Specification 1 561 518, in the monograph "H. Schnell, Chemistry and Physics of Polycarbonates, Interscience Publishers, New York 1964" and in JP-A 62039/1986, 62040/1986 and 105550/1986.

In the case of the homopolycarbonates only one diphenol is employed, and in the case of the copolycarbonates several diphenols are employed.

Molding compositions which comprise at least one polycarbonate with diol units from BPA and/or trimethylcyclohexyl-bisphenol (TMC), preferably selected from the group consisting of homopolymers of BPA, copolymers of BPA with TMC or copolymers with 5 to 60 wt. % TMC, are preferably used.

Suitable carbonic acid derivatives are, for example, phosgene or diphenyl carbonate.

Suitable chain terminators are both monophenols and monocarboxylic acids. Suitable monophenols are phenol itself, alkylphenols, such as cresols, p-tert-butylphenol, p-n-octylphenol, p-iso-octylphenol, p-n-nonylphenol and p-iso-nonylphenol and p-cumylphenol, halogenophenols, such as p-chlorophenol, 2,4-dichlorophenol, p-bromophenol, amylphenol and 2,4,6-tribromophenol, and mixtures thereof.

Preferred chain terminators are the phenols of the formula (I)

wherein R is hydrogen, tert-butyl or a branched or unbranched $C_8$- and/or $C_9$-alkyl radical. However, p-cumylphenol may also preferably be used. In the case of the transesterification process, the chain terminator results from the diaryl carbonate employed.

The amount of chain terminator to be employed, preferably in the phase boundary process, is 0.1 mol % to 5 mol %, based on the moles of the particular diphenols employed. The addition of the chain terminator may take place before, during or after the phosgenation.

Suitable branching agents are the compounds which are trifunctional or more than trifunctional and are known in polycarbonate chemistry, in particular those with three or more than three phenolic OH groups.

Suitable branching agents are, for example, phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-[4,4-bis-(4-hydroxyphenyl)-cyclohexyl]-propane, 2,4-bis-(4-hydroxyphenyl-isopropyl)-phenol, 2,6-bis-(2-hydroxy-5'-methyl-benzyl)-4-methylphenol, 2-(4-hydroxyphenyl)-2-(2,4-dihydroxyphenyl)-propane, hexa-(4-(4-hydroxyphenyl-isopropyl)-phenyl)-orthoterephthalic acid ester, tetra-(4-hydroxyphenyl)-methane, tetra-(4-(4-hydroxyphenyl-isopropyl)-phenoxy)-methane and 1,4-bis-(4',4''-dihydroxytriphenyl)-methyl)-benzene, as well as 2,4-dihydroxybenzoic acid, trimesic acid, cyanuric chloride and, for some uses, even preferably 3,3-bis-(3-methyl-4-hydroxyphenyl)-2-oxo-2,3-dihydroindole.

The amount of branching agents which are optionally to be employed is 0.01 mol % to 2 mol %, again based on the moles of the particular diphenols employed.

In the phase boundary process, the branching agents either may be initially introduced into the reaction vessel with the diphenols and the chain terminators in the aqueous alkaline phase, or may be added as a solution in an organic solvent. In the case of the transesterification process the branching agents may be employed together with the diphenols.

All these measures for the preparation of the thermoplastic polycarbonates are familiar to the expert.

The thermoplastic polymer mixtures according to the invention may furthermore comprise conventional additives for polycarbonates in the known amounts, such as, by way of example and preferably, stabilizers against UV radiation, flameproofing agents, dyestuffs, fillers, foams, optical brighteners and antistatics.

Those components which do not adversely influence the transparency of the material are preferably taken for optical uses.

These substances are to be found in many publications, such as, for example, in Additives for Plastics Handbook, John Murphy, 1999, and are commercially obtainable.

1. Suitable antioxidants are, for example:

1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphpenol, nonylphenols which are linear or branched in the side chain, for example 2,6-dinonyl-4-methylphenol, 2,4-dimethyl-6-(1'-methylundec-1'-yl)phenol, 2,4-dimethyl-6-(1'-methylheptadec-1'-yl)phenol and 2,4-dimethyl-6-(1'-methyltridec-1'-yl)phenol.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-(6-α-methylcyclohexyl)phenol)], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmeraptobutane, ethylene glycol bis[3,3-bis(3'-tert-butyl-4'-hydroxyphenyl) butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane and 1,1,5,5-tetra-(5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide and isooctyl 3,5-di-tert-butyl-4-hydroxybenzylmercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecylmercatoethyl 2,2-bis(3,5-di-tert-butyl-4-hydroxybenzyl)malonate and bis[4-(1,1,3,3-tetramethylbutyl) phenyl]2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2, 3,5,6-tetramethylbenzene and 2,4,6-tris(3,5-di-tert-butyl-4-hydroxybenzyl)-phenol.

1.10. Triazine compounds, for example 2,4-bis(octylmercapto)-6-3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4, 6-tris(3,5-di-tert-butyl-4-hydroxy-phenylethyl)-1,3,5-triazine, 1,3,5-tris(3,5-di-tert-butyl-4-hydroxyphenylpropionyl)-hexahydro-1,3,5-triazine and 1,3, 5-tris(3,5-dicyclohexyl-4-hydroxybenzyl) isocyanurate.

1.11. Acylaminophenols, for example 4-hydroxylauranilide, 4-hydroxystearanilide and octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentylglycol, thiodiethylene glycol, diethylene glycol triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane; the ester with octadecanol (IRGANOX 1076® from Ciba Spec.) is very particularly suitable and preferred here.

1.13. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentylglycol, thiodiethylene glycol, diethylene glycol triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.14. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentylglycol, thiodiethylene glycol, diethylene glycol triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.15. Esters of 3,5-di-tert-butyl-4-hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentylglycol, thiodiethylene glycol, diethylene glycol triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo [2.2.2]octane.

1.16. Amides of β-(3,5-di-tert-butyl-4-hydroxyphenyl) propionic acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide and N,N'-bis[2-(3-[3,5-di-tert-butyl-4-hydroxyphenyl]propionyloxy)ethyl]oxamide (Naugard® XL-1 from Uniroyal).

1.17. Ascorbic acid (vitamin C)

1.18. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyl-diphenylamine, 4-n-butylaminophenol, 4-butyrylaminophenol, 4-nonanoylaminophenol, 4-dodecanoylamino-phenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetremethylpiperid-4-ylhexamethylenediamine, bis(2,2,6,6-tetramethylpiperid-4-yl) sebacate, 2,2,6,6-tetramethylpiperidin-4-one and 2,2,6,6-tetramethylpiperidin-4-ol. Individual compounds of these or mixtures thereof may be employed.

1.19 Suitable thio-synergists are, for example, dilauryl thiodipropionate and/or distearyl thiodipropionate.

2. UV absorbers and light stabilizers may be employed in the compositions according to the invention in amounts of 0.1 to 15 wt. %, preferably 3 to 8 wt. %, based on the weight of the composition. Suitable UV absorbers and light stabilizers are, for example:

2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenylbenzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3', 5'-di-tert-amyl-2'-hydroxyphenyl)benzotriazole, 2-(3',5'-bis (α,α-dimethylbenzyl)-2'-hydroxyphenyl)benzotriazole, 2-(3'-tert-butyl-2'-hydroxy-5'-(2-octyloxycarbonyl-ethyl) phenyl)-5-chlorobenzotriazole, 2-(3'-tert-butyl-5'-[2-(2-ethylhexyloxy)carbonyl-ethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxycarbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenyl)benzotriazole, 2,2'-methylenebis[4-(1,1,3,3-tetramethylbutyl)-6-benzotriazol-2-ylphenol]; the transestification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, wherein R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole and 2-[2'-hydroxy-3'-(1,1,3,3-tetramethylbutyl)-5'-(α,α-dimethylbenzyl)phenyl] benzotriazole.

2.2 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3 Esters of substituted and unsubstituted benzoic acids, such as, for example, 4-tert-butylphenyl salicylate, phenyl salicylate, octylphenyl salicylate, dibenzoylresorcinol, bis (4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate 2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)]phenol], such as the 1:1 or 1:2 complex, with or without additional ligands, such as n-butylamine, triethanolamine or N-cyclohexyldiethanolamine, nickel dibutyldithiocarbamate, nickel salts of monoalkyl esters, e.g. of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, and nickel complexes of 1-phenyl-4-lauroyl-5-hydroxypyrazole, with or without additional ligands.

2.6 Sterically hindered amines, for example bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl), n-butyl 3,5-di-tert-butyl-4-hydroxybenzyl-malonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl) nitrilotriacetate, tetrakis(2, 2,6,6-tetramethyl-4-piperidyl) 1,2,3,4-butanetetracarboxylate, 1.1'-(1,2-ethanediyl) bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-bis(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3, 5-triazine, a condensation product of 1,2-bis(3-aminopropylamino)ethane and 2,4,6-trichloro-1,3,5-triazine as well as 4-butylamino-2,2,6,6-tetramethylpiperidine (CAS reg. no. [136504-96-6]; N-(2,2,6,6-tetramethyl-4-piperidyl)-n-dodecyl-succinimide, N-(1,2,2,6,6-pentamethyl-4-piperidyl)-n-dodecyl-succinimide, 2-undecyl-7,7,9,9-tetramethyl-1-oxa-3,8-diaza-4-oxospiro[4.5]decane, a reaction product of 7,7, 9,9-tetramethyl-2-cycloundecyl-1-oxa-3,8-diaza-4-oxospiro [4.5]decane and epichlorohydrin, 1,1-bis(1,2,2,6,6-pentamethyl-4-piperidyloxycarbonyl)-2-(4-methoxyphenyl) ethene, N,N'-bis(formyl)-N,N'-bis(2,2,6,6-tetramethyl-4-piperidyl)hexamethylenediamine, diesters of 4-methoxymethylenemalonic acid with 1,2,2,6,6-pentamethyl-4-hydroxypiperidine, poly[methylpropyl-3-oxy-4-(2, 2,6,6-tetramethyl-4-piperidyl)]siloxane and a reaction product of maleic anhydride/α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and a mixture thereof with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4, 6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-methoxyphenyl)-6-phenyl-1,3,5-triazine and 2-{2-hydroxy-4-[3-(2-ethylhexyl-1-oxy)-2-hydroxypropyloxy]phenyl}-4,6-bis(2,4-dimethylphenyl)-1,3,5-triazine.

Individual compounds of these or mixtures thereof may be employed.

3. Suitable metal deactivators are, for example, N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyldihydrazide, oxanilide, isophthaloyldihydrazide, sebacoylbisphenylhydrazide, N,N'-diacetyladipoyldihydrazide, N,N'-bis(salicyloyl)oxalyldihydrazide and N,N'-bis(salicyloyl)thiopropionyldihydrazide. Individual compounds of these or mixtures thereof may be employed.

4. Suitable peroxide-trapping agents are, for example, esters of β-thiodipropionic acid, for example the lauryl, stearyl, myristyl or tridecyl ester, mercaptobenzimidazole or the zinc salt of 2-mercaptobenzimidazole, zinc dibutyldithiocarbamate, dioctadecyl disulfide and pentaerythritol tetrakis(dodecylmercapto)propionate. Individual compounds of these or mixtures thereof may be employed.

5. Suitable basic costabilizers are, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate. Individual compounds of these or mixtures thereof may be employed.

6. Suitable nucleating agents are, for example, inorganic substances, such as talc, metal oxides, such as titanium dioxide or magnesium oxide, phosphates, carbonates or sulfates, preferably of alkaline earth metals; organic compounds, such as mono- or polycarboxylic acids and salts thereof, e.g. 4-tert-butylbenzoic acid, adipic acid, diphenylacetic acid, sodium succinate or sodium benzoate; and polymeric compounds, such as ionic copolymers (ionomers). 1,3:2,4-Bis(3',4'-dimethylbenzylidene)sorbitol, 1,3:2, 4-di(paramethyldibenzylidene)sorbitol and 1,3:2,4-di(benzylidene)sorbitol are particularly preferred. Individual compounds of these or mixtures thereof may be employed.

7. Suitable fillers and reinforcing agents are, for example, calcium carbonate, silicates, glass fibres, glass balloons, asbestos, talc, kaolin, mica, barium sulfate, metal oxides and hydroxides, carbon black, graphite, wollastonite, wood flour and flours or fibres of other natural products and synthetic fibres. Individual compounds of these or mixtures thereof may be employed.

8. Other suitable additives are, for example, plasticizers, lubricants, emulsifiers, pigments, viscosity modifiers, catalysts, flow agents, optical brighteners, flameproofing agents, antistatic agents and blowing agents.

9. Suitable benzofuranones and indolinones are, for example, those which are disclosed in U.S. Pat. No. 4,325, 863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102, or 3-[4-(2-acetoxyethoxy)phenyl]-5,7-ditert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one and 3-(2,3-dimethylphenyl)-5,7-di-tert-butylbenzofuran-2-one; and lactone antioxidants such as (8)

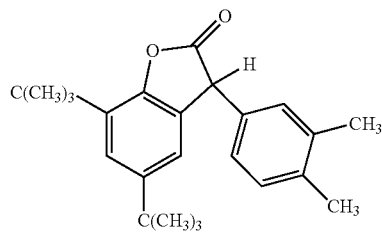

These compounds act, for example, as antioxidants. Individual compounds of these or mixtures thereof may be employed.

10. Suitable fluorescent plasticizers are those listed in "Plastics Additives Handbook", eds. R. Gächter and H. Müller, Hanser Verlag, 3rd ed., 1990, page 775-789.

11. Suitable flame-retardant additives are phosphate esters, i.e. triphenyl phosphate, resorcinol-diphosphoric acid esters, bromine-containing compounds, such as brominated phosphoric acid esters, brominated oligocarbonates and polycarbonates, and salts, such as $C_4F_9SO_3^-Na^+$.

12. Suitable impact modifiers are butadiene rubber with grafted-on styrene-acrylonitrile or methyl methacrylate, ethylene-propylene rubbers with grafted-on maleic anhydride, ethyl and butyl acrylate rubbers with grafted-on methyl methacrylate or styrene-acrylonitrile and interpenetrating siloxane and acrylate networks with grafted-on methyl methacrylate or styrene-acrylonitrile.

13. Suitable polymers are SAN, ABS, PMMA, PTFE, PSU, PPS, polyolefins, such as polyethylene, polypropylene and ethylene-propylene rubbers, epoxy resins, polyesters, such as PBT, PET, PCT, PCTG and PETG, and other polycarbonates produced in the interfacial process.

14. Suitable antistatic agents are sulfonate salts, for example tetraethylammonium salts of $C_{12}H_{25}SO^{3-}$ or $C_8F_{17}SO^{3-}$.

15. Suitable colouring agents are pigments and organic and inorganic dyestuffs.

16. Compounds which contain epoxide groups, such as 3,4-epoxycyclohexylmethyl 3,4-epoxycyclohexylcarboxylate and copolymers of glycidyl methacrylate and epoxysilanes.

17. Compounds which contain anhydride groups, such as maleic anhydride, succinic anhydride, benzoic anhydride and phthalic anhydride.

18. Phosphites and phosphonites which are suitable as stabilizers are, for example, triphenyl phosphite, diphenyl alkyl phosphites, phenyl dialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocine, 2,2',2"-nitrilo [triethyl tris(3,3',5,5'-tetra-tert-butyl-1,1'-biphenyl-2,2'-diyl)-phosphite], 2-ethyl-hexyl(3,3',5,5'-tetra-tert-butyl-1,1'-biphenyl-2,2'-diyl)-phosphite and 5-butyl-5-ethyl-2-(2,4,6-tri-tert-butylphenoxy)-1,3,2-dioxaphosphirane. Individual compounds of these or mixtures thereof may be employed.

Tris(2,4-di-tert-butylphenyl) phosphite (Irgafos® 168, Ciba-Geigy) or triphenylphosphine are particularly preferred.

The compounds of groups 16 and 17 act as melt stabilizers. They may be employed individually or in mixtures.

Esters of mono- or polyhydric alcohols with long-chain carboxylic acids, such as Loxiol G32 or Loxiol G33, are preferably used as mold release agents. Those mold release agents which have not been completely esterified and accordingly contain free OH groups are also preferred. (Partial) esters of saturated monobasic fatty acids having 16 to 22 carbon atoms with glycerol, trimethylolpropane, pentaerythritol or similar polyhydric alcohols are particularly preferred, in particular glycerol monostearate (GMS) and glycerol monopalmitate. Pentaerythritol tetrastearate (PETS) is furthermore preferred.

Such saturated monofunctional fatty acid esters of glycerol are employed by themselves or as mixtures with two or more components. The saturated monoesters of glycerol are conventionally prepared via transesterification of hydrogenated animal or vegetable oil with glycerol. Although the reaction product may also contain esters other than the glycerol esters, it is employed as a mold release agent. For example, the mixture may contain small or larger contents of diglycerides and triglycerides.

The optimum amount of mold release agent in the production of CDs and other optical storage media (DVDs etc.) is determined on the one hand by an adequate mold release action, and on the other hand by the formation of a deposit on the mold. Concentrations which are conventionally employed are between 50 to 1,000 ppm, more advantageously between 100 and 500 ppm of mold release agent. For the other uses of polycarbonate the concentrations are 100-10,000 ppm, preferably 2,000-7,000 ppm.

Specific phosphites which have both aromatic and aliphatic radicals in one molecule are used, for example but not by way of limitation, as heat stabilizers. These are compounds of the following structure:

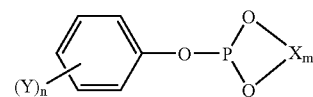

wherein n represents the number 0-5, preferably 1-3 and very particularly preferably represents 3, Y in each case independently of one another, denotes alkyl or optionally substituted aryl, preferably $C_1$-$C_4$-alkyl, particularly preferably methyl, sec-butyl and tert-butyl, m represents the number 1-3, preferably 3 and X in each case independently of one another, represents an optionally substituted methylene radical, wherein at least one methylene radical must be completely substituted and the substituents independently of one another are selected from the group consisting of $C_1$-$C_{20}$-alkyl, or the two substituents on a completely substituted methylene radical together represent a radical

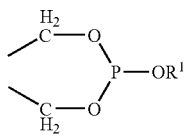

in which $R^1$ is selected from the group consisting of $C_1$-$C_{18}$-alkyl, $C_3$-$C_{12}$-cycloalkyl, $C_6$-$C_{30}$-alkaryl and aryl, wherein these radicals in turn may be substituted by 1-4 O-alkylene-O and/or carboxylic acid ester COO radicals; $C_2$-$C_{18}$-polyhydroxyalkyl having 2 to 10 hydroxyl groups; and $C_2$-$C_{18}$-polyphenyl radicals having 2 to ten phenolic OH groups.

Preferred compounds here are those of the formula

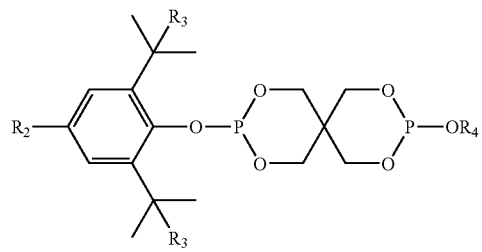

in which
$R_2$ represents $C_1$-$C_6$-alkyl;
$R_3$ represents methyl or ethyl and
$R_4$ is selected from the group consisting of $C_1$-$C_{18}$-alkyl, $C_3$-$C_{12}$-cycloalkyl, $C_6$-$C_{30}$-alkaryl and aryl, wherein these radicals in turn may be substituted by 1-4 O-alkylene-O and/or carboxylic acid ester COO radicals; $C_2$-$C_{18}$-polyhydroxyalkyl having 2 to 10 hydroxyl groups; and $C_2$-$C_{18}$-polyphenyl radicals having 2 to 10 phenolic OH groups.

Compounds which are also preferred are those of the formula

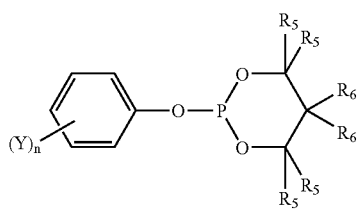

wherein Y and n have the abovementioned meanings and
$R_5$ independently of one another, is selected from the group consisting of hydrogen and $C_3$-$C_{20}$-alkyl, and preferably at least one $R_5$ here represents alkyl, and
$R_6$ independently of one another represent $C_1$-$C_{10}$-alkyl.

Particularly preferred compounds are those of the formula

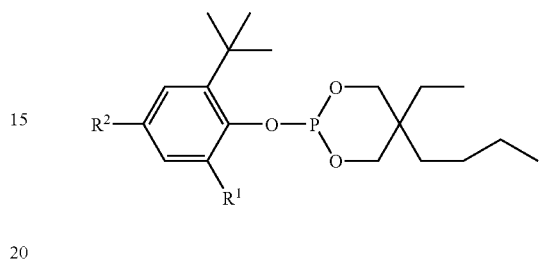

wherein $R^1$ and $R^2$ represent methyl, sec-butyl or tert-butyl.

Compounds which are also particularly preferred are moreover those defined in EP A1 0 038 876 on p. 16-20 and the example mentioned on page 21 in the same specification.

(2,4,6-Tri-t-butylphenyl) (2-butyl-2-ethyl-propane-1,3-diyl) phosphite is very particularly preferred, this having the following structure:

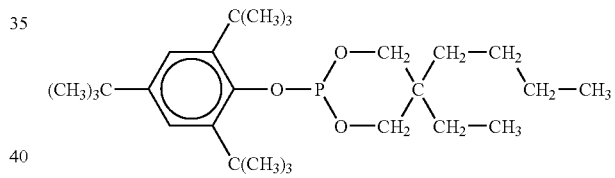

The phosphites may be employed by themselves, but also in combination with other phosphorus compounds, it also being possible for the other phosphorus compounds to be those which have a different oxidation number for the phosphorus. Accordingly e.g. combinations of the phosphites according to the invention with other phosphites, with phosphines, e.g. triphenylphosphine, with phosphonites, with phosphates, with phosphonates etc. may be employed.

The phosphites employed are generally known or may be prepared analogously to known phosphites. (2,4,6-Tri-t-butylphenyl) (2-butyl-2-ethyl-propane-1,3-diyl) phosphite is described e.g. in EP-A 702018 and EP 635514.

The polymer mixtures according to the invention in general comprises the phosphorus compound in a content of 10-5,000 ppm, preferably 10-1,000 ppm, particularly preferably 20-500 ppm, very particularly preferably between 50 and 250 ppm.

The addition of the mold release agents, the phosphorus compound and the formals according to the invention to the thermoplastic molding compositions takes place, by way of example and preferably, by a procedure in which they are metered in after the preparation and during the working up of the polycarbonates, e.g. by addition to the polycarbonate polymer solution, or into a melt of the thermoplastic molding compositions. It is furthermore also possible to meter in the components independently of one another in various working steps, e.g. one of the components during the working up of the polymer solution and the other component(s) into the melt, as long as it is ensured that all the components are contained during the production of the end products (molded articles). For uses in the CD, DVD and other optical recording media sector, the expert will of course choose, from the abovementioned additives, suitable additives which do not impair the transparency.

Very particularly suitable additives are IRGANOX 1076®, see above, and benzotriazoles of group 2.1 (so-called Tinuvins), in particular in a mixture with one another and triphenylphosphine (TPP).

The molding compositions according to the invention are used for the production of molded articles, preferably optical media, in particular for the production of compact discs and DVDs as well as optical media which may be written to and deleted once or several times, in the manner known for polycarbonates. The layers which may be written to here comprise in particular dyestuffs or metallic layers, the latter using the change from the amorphous into the crystalline state as the recording principle or having magnetic properties.

This production of the optical media is preferably carried out from the finished prepared molding compositions according to the invention, which are obtained, for example, as granules. However, the optical media may also be produced by incorporation of the components into pure or commercially available polycarbonates and/or into the conventional additives in the production of molded articles from polycarbonates.

The invention accordingly also provides molded articles, such as, in particular, optical data carriers, preferably compact discs and DVDs, which are obtainable from the thermoplastic molding compositions according to the invention.

The thermoplastic molding compositions according to the invention have the advantage that they have a relatively low water uptake and therefore an improved dimensional stability. They are furthermore distinguished by improved flow properties, since they have a relatively low melt viscosity.

The following examples serve to explain the invention. The invention is not limited to the examples.

EXAMPLES

Synthesis of the Aromatic Formals

Example 1

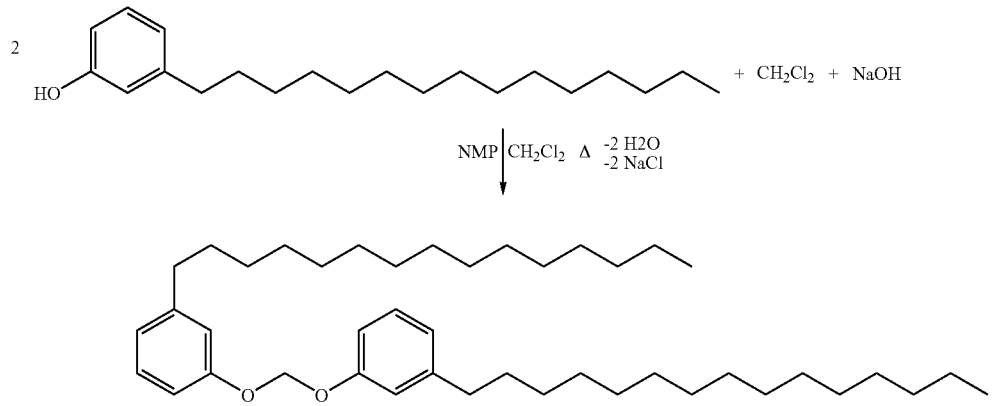

50.0 g (0.16 mol) distilled 3-pentadecylphenol and 16.0 g (0.40 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 44.8 g (90.2% of theory) of a waxy solid were obtained.

Analysis: $^1$H-NMR (400 MHz, TMS, CDCl$_3$) δ=7.2-6.82 (m, 8H), 5.68 (s, 2H), 2.58-2.54 (m, 4H), 1.62-1.57 (m, 4H), 1.39-1.20 (m, 48H), 0.89-0.86 (t, 6H).

Example 2

Analogous to example 1, but 4 times the batch size.
Yield: 181.6 g (91.4% of theory) Analysis: analogous NMR spectrum to that under example 1

Example 3

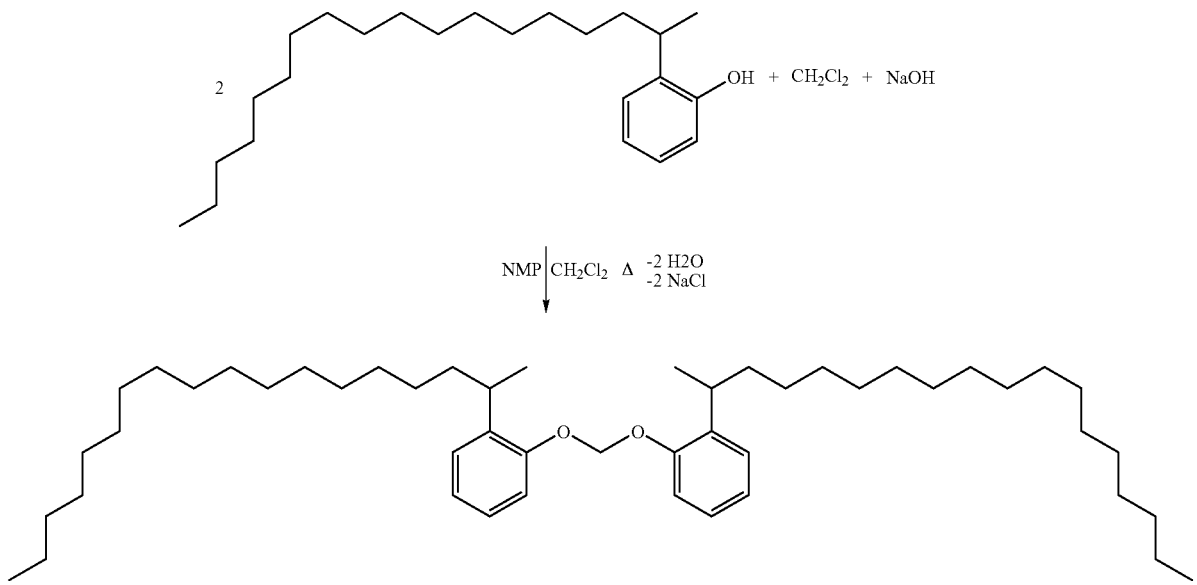

50.0 g (0.14 mol) octadecylphenol and 14.4 g (0.36 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 42.0 g (85.1% of theory) of a waxy solid were obtained.

Analysis: $^1$H-NMR (400 MHz, TMS, CDCl$_3$) δ=7.22-6.97 (m, 8H), 5.7 (s, 2H), 3.15-3.05 (m, 2H), 1.55-0.9 (m, 36H), 0.85-0.81 (t, 6H).

Example 4

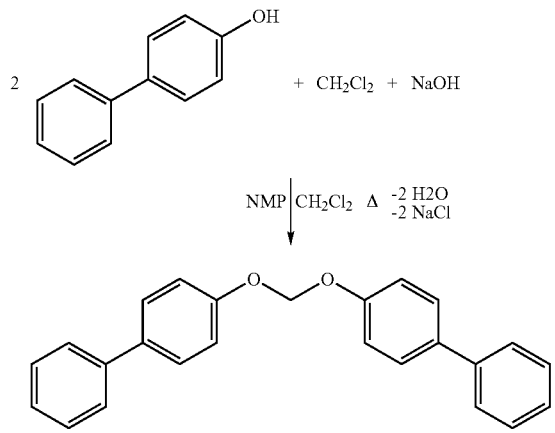

23.8 g (0.14 mol) 4-hydroxybiphenyl and 14.4 g (0.36 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 21.7 g (87.9% of theory) of a white solid were obtained.

Analysis: $^1$H-NMR (400 MHz, TMS, CDCl$_3$) δ=7.65-7.5 (m, 8H), 7.45-7.35 (m, 4H), 7.35-7.25 (m, 2H), 7.25-7.15 (m, 4H), 5.8 (s, 2H).

Example 5

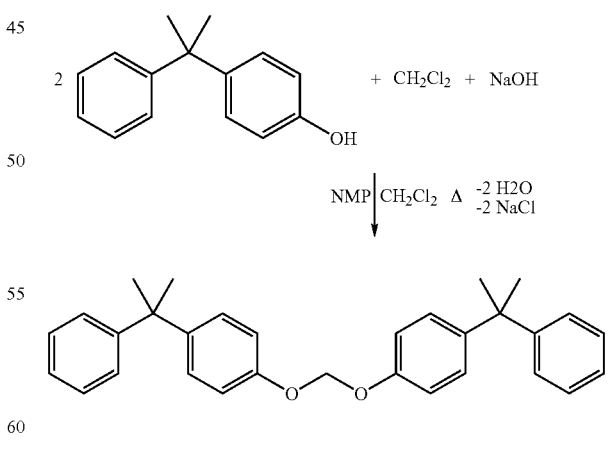

29.7 g (0.14 mol) 4-cumylphenol and 14.4 g (0.36 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 21.5 g (70.3% of theory) of a white solid were obtained.

Analysis: $^1$H-NMR (400 MHz, TMS, CDCl$_3$) δ=7.28-7.19 (m, 8H), 7.19-7.09 (m, 6H), 7.05-6.95 (m, 4H), 5.68 (s, 2H), 1.65 (s, 12H).

Example 6

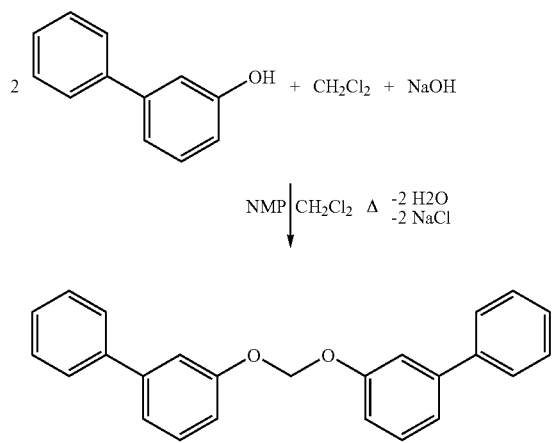

23.8 g (0.14 mol) 3-hydroxybiphenyl and 144 g (0.36 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 14.2 g (57.6% of theory) of a white solid were obtained.

Analysis: $^1$H-NMR (400 MHz, TMS, CDCl$_3$) δ=7.6-7.5 (m, 4H), 7.5-7.2 (m, 12H), 7.15-7.05 (m, 2H), 5.85 (s, 2H).

Example 7

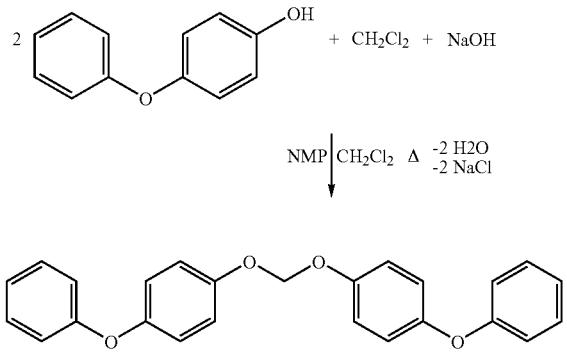

24.2 g (0.13 mol) 4-hydroxydiphenyl ether and 13.0 g (0.325 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in a methanol/water mixture (1:1). The crude product obtained was finally rinsed several times with water and in conclusion dried at 80° C. in a vacuum drying cabinet. 21.0 g (84.0% of theory) of a white solid were obtained.

Analysis: $^1$H-NMR (400 MHz, TMS, CDCl$_3$) δ=7.35-7.22 (m, 4H), 7.15-7.02 (m, 6H), 7.02-6.9 (m, 8H), 5.65 (s, 2H).

Example 8

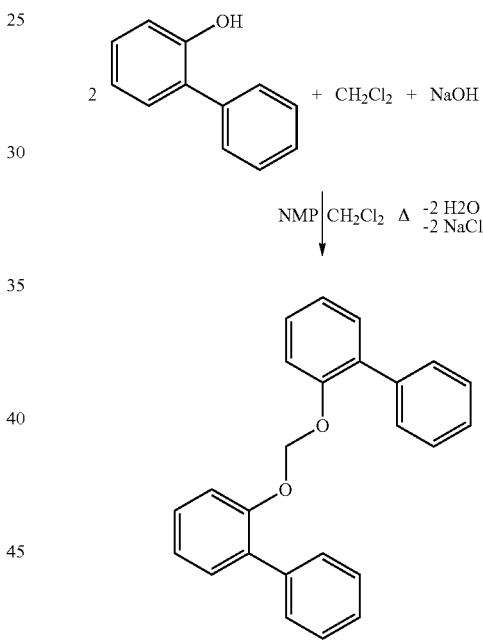

23.8 g (0.14 mol) 4-cumylphenol and 14.4 g (0.36 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 13.0 g (52.7% of theory) of a white solid were obtained.

Analysis: $^1$H-NMR (400 MHz, TMS, CDCl$_3$) δ=7.45-7.15 (m, 16H), 7.15-7.05 (m, 2H), 5.58 (s, 2H).

Example 9

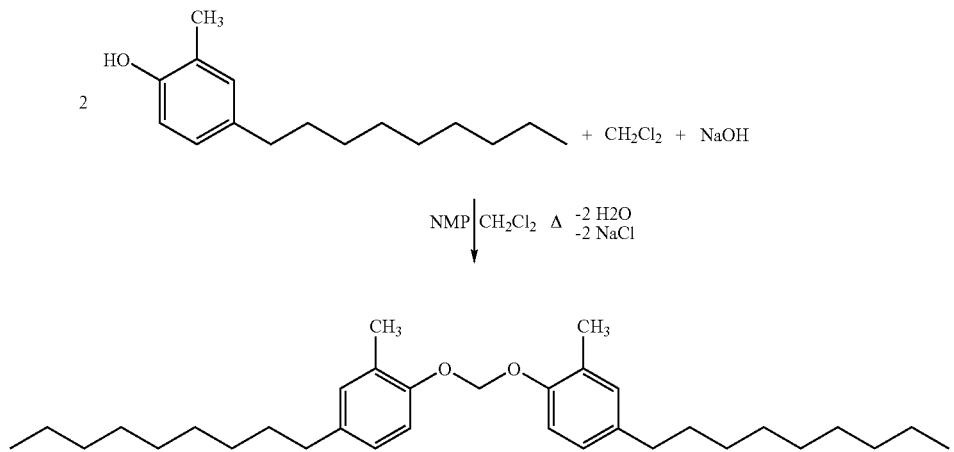

50.0 g (0.21 mol) 2-methyl-4-nonylphenol and 21.3 g (0.53 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 9.4 g (18.6% of theory) of a highly viscous substance were obtained.

Analysis: $^1$H-NMR (400 MHz, TMS, CDCl$_3$) δ=7.1-6.9 (m, 6H), 5.65 (s, 2H), 2.12 (s, 6H), 1.7-0.45 (m, 38H).

Example 10

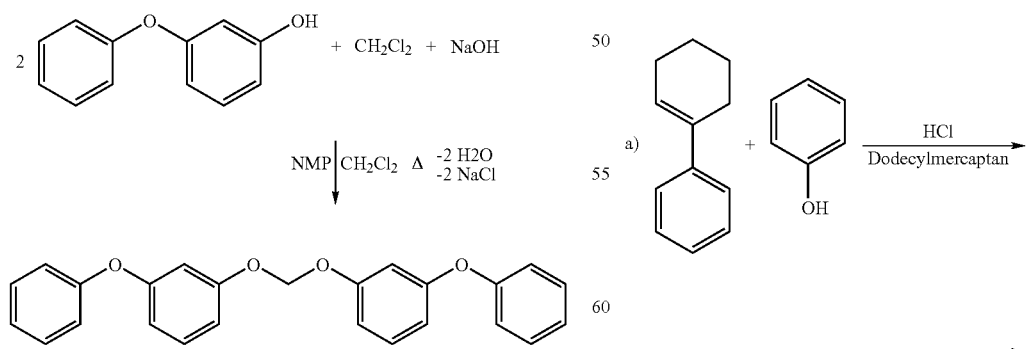

17.4 g (0.093 mol) 3-hydroxydiphenyl ether and 9.3 g (0.23 mol) sodium hydroxide (microprills from Riedel) are added to a mixture of 100 ml methylene chloride and 180 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The organic phase was then concentrated. The crude product obtained was finally rinsed several times with water and in conclusion dried under a high vacuum at 160° C. 15.7 g (90.7% of theory) of a highly viscous substance were obtained.

Analysis: $^1$H-NMR (400 MHz, TMS, CDCl$_3$) δ=7.45-7.35 (m, 4H), 7.35-7.2 (m, 2H), 7.2-7.1 (m, 2H), 7.1-7.0 (m, 4H), 6.9-6.8 (m, 2H), 6.8-6.7 (m, 2H), 6.7-6.6 (m, 2H), 5.82 (s, 2H).

Example 11

-continued

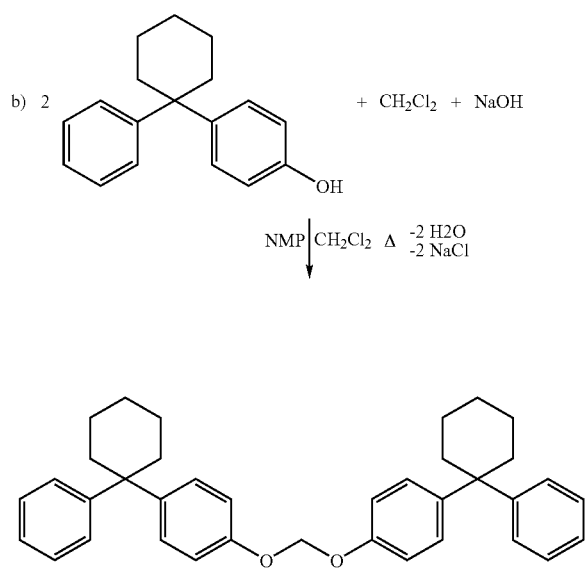

Example 12

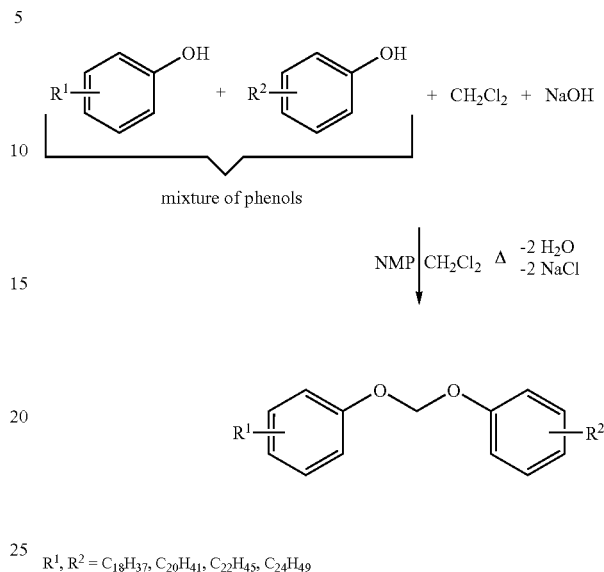

$R^1, R^2 = C_{18}H_{37}, C_{20}H_{41}, C_{22}H_{45}, C_{24}H_{49}$ a) 24 g (0.15 mol) 1-phenyl-1-cyclohexene (Aldrich) and, in a large excess, 56.5 g (0.60 mol) freshly distilled phenol are initially introduced into the reaction vessel, and 0.3 g (0.0015 mol) dodecylmercaptan is added to the reaction batch as a catalyst. Passing in of gaseous hydrogen chloride is started at a temperature of 30° C. This is maintained for 20 minutes in total. After the mixture had solidified the excess phenol was distilled off under a water pump vacuum. The last residues of phenol could be distilled of at 120° C. under a high vacuum. 36.5 g (96.4% of theory) of a white solid are obtained.

Analysis: $^1$H-NMR (400 MHz TMS, CDCl$_3$) δ=9.12 (s, 1H), 7.3-7.15 (m, 4H), 7.15-7.0 (m, 3H), 6.7-6.6 (m, 2H), 2.2 (m, 4H), 1.45 (m, 6H).

b) 5 g (0.0198 mol) of the product from example 11a) and 1.98 g (0.05 mol) sodium hydroxide (microprills from Riedel) are added to a mixture of 30 ml methylene chloride and 55 ml N-methylpyrrolidone (NMP). The mixture was then boiled under reflux for 1 hour. After cooling of the reaction mixture, methylene chloride and water were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 3.7 g (72.3% of theory) of a white solid were obtained.

Analysis: $^1$H-NMR (400 MHz, TMS, CDCl$_3$) δ=7.3-7.2 (m, 8), 7.2-7.15 (m, 4H), 7.15-7.05 (m, 2H), 7.0-6.9 (m, 4H), 5.65 (s, 2H), 2.25 (m, 8H), 1.65-1.45 (m, 12H).

50.0 g AP 2024, a mixture of phenols as shown by the formulae, (Idemitsu Petrochemicals Co. Ltd., Tokyo, Japan) and 13.2 g (0.33 mol) sodium hydroxide (microprills from Riedel) are added to a mixture of 125 ml methylene chloride and 225 ml N-methylpyrrolidone (NMP). The mixture was then boiled under reflux for 1 hour. After cooling of the reaction mixture, methylene chloride and water mixture of phenols were added until an adequate phase separation was reached. The organic phase was separated off and washed several times with water to the neutral point. The dried organic phase was then precipitated in methanol. The crude product obtained was finally rinsed several times with methanol and in conclusion dried at 80° C. in a vacuum drying cabinet. 30.5 g of a highly viscous substance were obtained.

Analysis: $^1$H-NMR (400 MHz, TMS, CDCl$_3$) δ=7.2-6.9 (m, H$_{ar}$), 5.75-5.65 (m, H$_{OCH2}$), 1.7-0.7 (m, H$_{alk}$).

The formals obtained as shown above were evaluated as to their efficacy as additives in the following polycarbonate types:

Makrolon® CD2005 (Bayer AG) homopolycarbonate for optical storage media based on bisphenol A, MFR 63 g/10 min, easily removable from the mold, injection molding)

Apec 1800 (Bayer AG,) co-polycarbonate type based on bisphenol A and TMC-bisphenol; base type softening temperature (VST/B 120)=185° C.)

The water content of the polycarbonate is determined after storage in humid climate at a relative humidity of 95% and 30° C. of storage temperature. The water content is determined directly before storage and after 7 and 14 days by means of Karl-Fischer-titration (coulometric titration).

| Structure of Formal | Polymer | formal of example 4 [wt. %] | Tg | directly | after 7 days | after 14 days |
|---|---|---|---|---|---|---|
| (4-phenylphenyl)-O-CH2-O-(4-phenylphenyl) — Example 4 | Makrolon with CD2005 | 1.0 | 137 | 0.04 0.05 | 0.21/0.24 | 0.20/0.28 |
| | Makrolon with CD2005 | 2.0 | 132 | 0.02/0.03 0.04 | 0.20/0.22 | 0.21/0.29 |
| | Makrolon with CD2005 | 3.0 | 128 | | 0.17/0.25 | 0.17/0.28 |
| | Apec 1800 with | 1.0 | 176 | | 0.31/0.32 | 0.28/0.33 |
| | Apec 1800 with | 2.0 | | | | |
| | Apec 1800 with | 3.0 | | | | |

| Structure of Formal | Polymer | Formal of example 6 [wt. %] | Tg | directly | after 7 days | after 14 days |
|---|---|---|---|---|---|---|
| (3-phenylphenyl)-O-CH2-O-(3-phenylphenyl) — Example 6 | Makrolon with CD2005 | 3.0 | 127 | 0.03 | 0.12/0.25 | 0.15/0.23 |
| | Apec 1800 with | 3.0 | 165 | 0.03 | 0.23/0.26 | 0.23/0.25 |

Water uptake [wt. %] of polycarbonate with formals as additives

| Structure of Formal | Polymer | formal of example 1 [wt. %] | Tg [° C.] | directly | after 7 days | after 14 days |
|---|---|---|---|---|---|---|
| C15H31-cyclohexyl-O-CH2-O-cyclohexenyl-C15H31 — Example 1 | Makrolon with CD2005 | 1.0 | 135 | 0.07% | 0.20...0.21% | 0.15...0.19% |
| | Makrolon with CD2005 | 2.0 | 128 | 0.03...0.04% | 0.18...0.19% | 0.14...0.23% |
| | Makrolon with CD2005 | 3.0 | 123 | 0.03/0.05 | 0.17/0.23 | 0.17/0.24 |
| | Apec 1800 with | 1.0 | 176 | 0.04 | 0.26/0.30 | 0.26/0.29 |
| | Apec 1800 with | 2.0 | 165 | 0.03/0.04 | 0.20/0.26 | 0.19/0.28 |
| | Apec 1800 with | 3.0 | 157 | 0.02/0.03 | 0.23/0.25 | 0.23/0.26 |

| Structure of Formal | Polymer | formal of example 3 [wt. %] | Tg (° C.) | directly | after 7 days | after 14 days |
|---|---|---|---|---|---|---|
| C16H33-CH(CH3)-(2-phenyl)-O-CH2-O-(2-phenyl)-CH(CH3)-C16H33 — Example 3 | Makrolon with CD2005 | 1.0 | 136 | 0.06% | 0.18...0.20% | 0.19...0.27% |
| | Makrolon with CD2005 | 2.0 | 130 | 0.07% | 0.14...0.26% | 0.15...0.24% |
| | Makrolon with CD2005 | 3.0 | 126 | 0.06% | 0.15...0.21% | 0.15...0.16% |
| | Apec 1800 with | 1.0 | 175 | 0.06...0.07% | 0.26...0.29% | 0.23...0.26% |
| | Apec 1800 with | 2.0 | 166 | 0.04...0.05% | 0.27...0.29% | 0.21...0.24% |
| | Apec 1800 with | 3.0 | 158 | 0.05% | 0.21...0.25% | 0.21...0.23% |

| Structure of Formal | Polymer | formal of example 7 [wt. %] | Tg | directly | after 7 days | after 14 days |
|---|---|---|---|---|---|---|
| (4-phenoxyphenyl)-O-CH2-O-(4-phenoxyphenyl) — Example 7 | Makrolon with CD2005 | 3.0 | 130 | 0.03 | 0.18/0.23 | 0.14/0.20 |
| | Apec 1800 with | 3.0 | 162 | 0.003 | 0.19/0.25 | 0.17/0.27 |

The following formals were employed in an analogous manner.

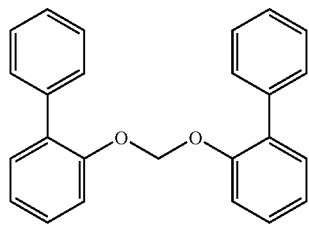

Example 8

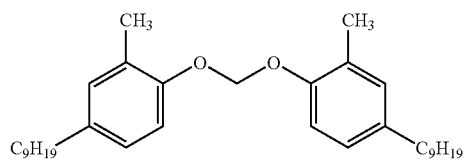

Example 9

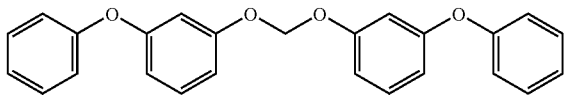

Example 10

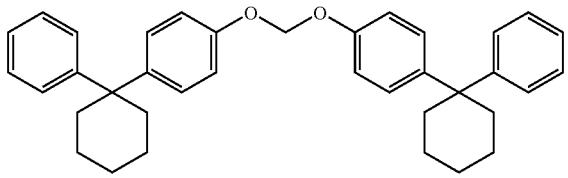

Example 11

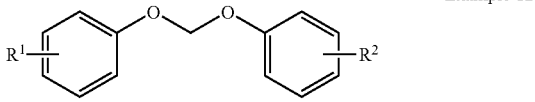

Example 12

$R^1, R^2 = C_{18}H_{37}, C_{20}H_{41}, C_{22}H_{45}, C_{24}H_{49}$

The results of the experiments show the surprising and completely unexpected action of the compounds according to the invention as additives which lower the water uptake (measured by the determination of water content) in polycarbonate. In contrast, the water content of unmodified polycarbonate compositions is of 0.32-0.34% for CD 2005 and 0.4% for Apec 1800.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

| Structure of Formal | Polymer | formal of example 4 [wt. %] | Tg | directly | after 7 days | after 14 days |
|---|---|---|---|---|---|---|
| (Example 4 structure) | Makrolon with CD2005 | 1.0 | 137 | 0.04 0.05 | 0.21/0.24 | 0.20/0.28 |
| | Makrolon with CD2005 | 2.0 | 132 | 0.02/0.03 0.04 | 0.20/0.22 | 0.21/0.29 |
| | Makrolon with CD2005 | 3.0 | 128 | | 0.17/0.25 | 0.17/0.28 |
| | Apec 1800 with | 1.0 | 176 | | 0.31/0.32 | 0.28/0.33 |
| | Apec 1800 with | 2.0 | | | | |
| | Apec 1800 with | 3.0 | | | | |

| Structure of Formal | Polymer | Formal of example 6 [wt. %] | Tg | directly | after 7 days | after 14 days |
|---|---|---|---|---|---|---|
| (Example 6 structure) | Makrolon with CD2005 | 3.0 | 127 | 0.03 | 0.12/0.25 | 0.15/0.23 |
| | Apec 1800 with | 3.0 | 165 | 0.03 | 0.23/0.26 | 0.23/0.25 |

-continued
Water uptake [wt. %] of polycarbonate with formals as additives

| Structure of Formal | Polymer | formal of example 1 [wt. %] | Tg [° C.] | directly | after 7 days | after 14 days |
|---|---|---|---|---|---|---|
| Example 1 | Makrolon with CD2005 | 1.0 | 135 | 0.07% | 0.20 ... 0.21% | 0.15 ... 0.19% |
| | Makrolon with CD2005 | 2.0 | 128 | 0.03 ... 0.04% | 0.18 ... 0.19% | 0.14 ... 0.23% |
| | Makrolon with CD2005 | 3.0 | 123 | 0.03/0.05 | 0.17/0.23 | 0.17/0.24 |
| | Apec 1800 with | 1.0 | 176 | 0.04 | 0.26/0.30 | 0.26/0.29 |
| | Apec 1800 with | 2.0 | 165 | 0.03/0.04 | 0.20/0.26 | 0.19/0.28 |
| | Apec 1800 with | 3.0 | 157 | 0.02/0.03 | 0.23/0.25 | 0.23/0.26 |

| Structure of Formal | Polymer | formal of example 3 [wt. %] | Tg (° C.) | directly | after 7 days | after 14 days |
|---|---|---|---|---|---|---|
| Example 3 | Makrolon with CD2005 | 1.0 | 136 | 0.06% | 0.18 ... 0.20% | 0.19 ... 0.27% |
| | Makrolon with CD2005 | 2.0 | 130 | 0.07% | 0.14 ... 0.26% | 0.15 ... 0.24% |
| | Makrolon with CD2005 | 3.0 | 126 | 0.06% | 0.15 ... 0.21% | 0.15 ... 0.16% |
| | Apec 1800 with | 1.0 | 175 | 0.06 ... 0.07% | 0.26 ... 0.29% | 0.23 ... 0.26% |
| | Apec 1800 with | 2.0 | 166 | 0.04 ... 0.05% | 0.27 ... 0.29% | 0.21 ... 0.24% |
| | Apec 1800 with | 3.0 | 158 | 0.05% | 0.21 ... 0.25% | 0.21 ... 0.23% |

| Structure of Formal | Polymer | formal of example 7 [wt. %] | Tg | directly | after 7 days | after 14 days |
|---|---|---|---|---|---|---|
| Example 7 | Makrolon with CD2005 | 3.0 | 130 | 0.03 | 0.18/0.23 | 0.14/0.20 |
| | Apec 1800 with | 3.0 | 162 | 0.003 | 0.19/0.25 | 0.17/0.27 |

What is claimed is:

1. A thermoplastic molding composition comprising polycarbonate and at least one aromatic formal conforming to the following structure

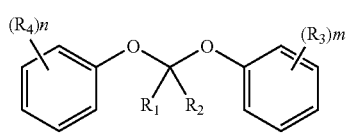

(1)

wherein $R_1$ and $R_2$ represent hydrogen or phenyl, $R_3$ and $R_4$ represent hydrogen, linear or branched $C_1$-$C_{40}$-alkyl or -alkoxy, aryl or aryloxy, or aralkyl and n and m independently of one another represent an integer, of 0 to 5.

2. The composition according to claim 1, further containing at least one mould release agent in the form of an ester of polyhydric alcohol with long-chain carboxylic acid, the ester containing at least one free OH group.

3. The composition according to claim 1 wherein the polycarbonate has a weight average molecular weight of 15,000 to 35,000.

4. The composition according to claim 1 wherein the aromatic formal is present in an amount of 10-60,000 ppm relative to the weight of the polycarbonate.

5. The composition according to claim 2 wherein the mold release agent is present in an amount of 0.01 to 1.5 wt. %.

6. The composition according to claim 1 further comprising a thermal stabilizer.

7. A molded article comprising the composition of claim 1.

8. An optical data storage comprising the composition of claim 1.

9. A compound selected from the group consisting of:
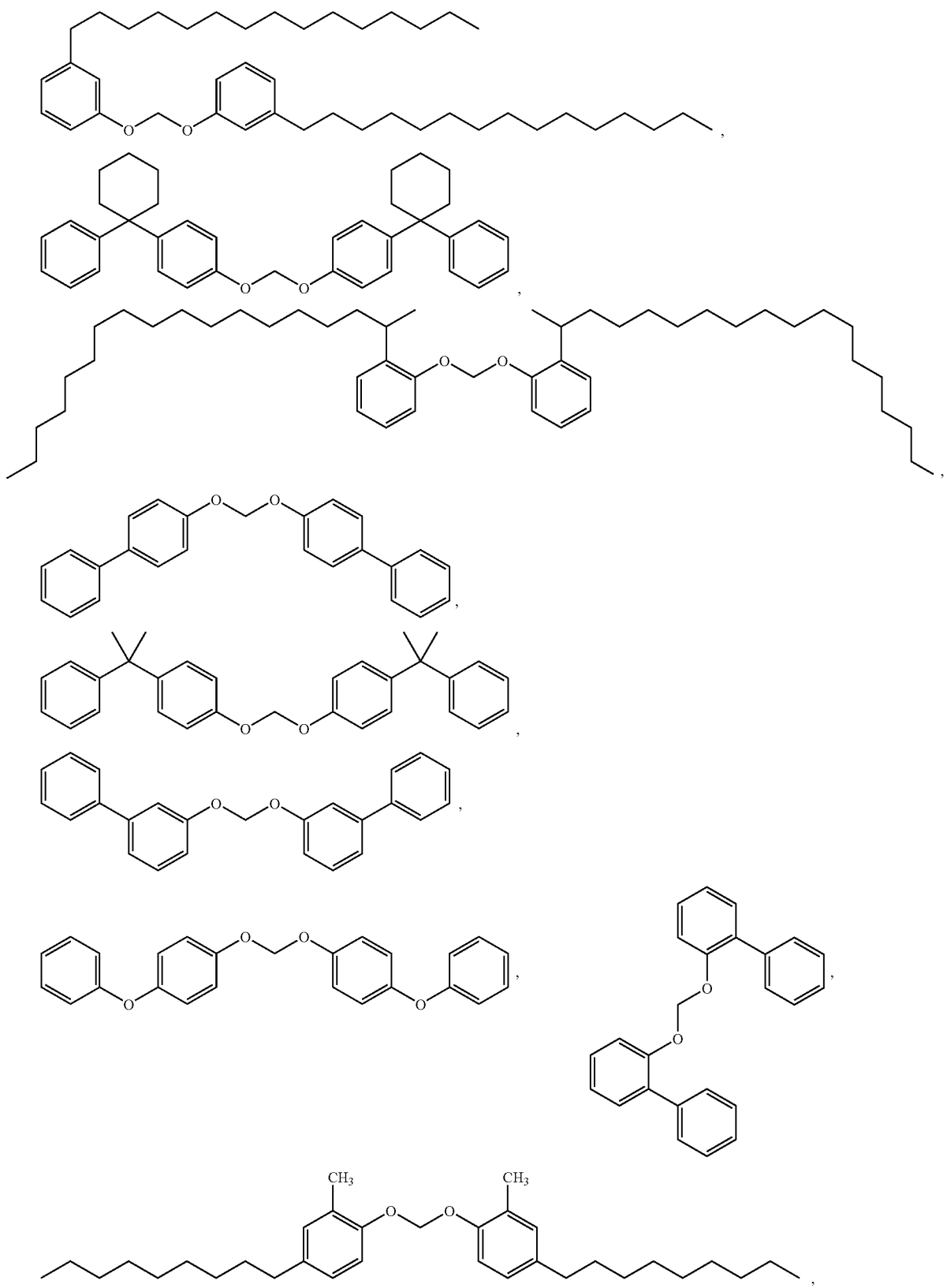

-continued
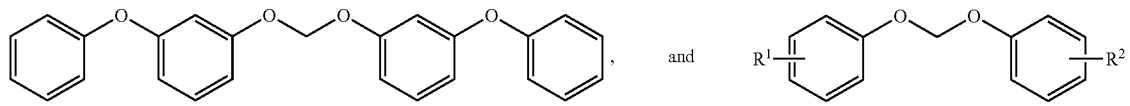
wherein $R^1$, $R^2 = C_{18}H_{37}$, $C_{20}H_{41}$, $C_{22}H_{45}$, $C_{24}H_{49}$.
* * * * *